United States Patent [19]
Ikada et al.

[11] Patent Number: 5,609,881
[45] Date of Patent: Mar. 11, 1997

[54] BIO-DEGRADABLE/ABSORBABLE BARRIER MEMBRANE

[75] Inventors: Yoshito Ikada; Shokyu Gen, both of Uji; Takao Kubota, Kamakura; Ikuo Kyotani, Kitamoto, all of Japan

[73] Assignees: GC Corporation, Tokyo; Biomaterials Universe Inc., Kyoto, both of Japan

[21] Appl. No.: 548,138

[22] Filed: Oct. 25, 1995

[30] Foreign Application Priority Data

Oct. 31, 1994 [JP] Japan .................................. 6-288692

[51] Int. Cl.$^6$ ............................ A61L 31/00; A61L 33/00; A61K 9/70
[52] U.S. Cl. ............................ 424/425; 424/424; 424/426
[58] Field of Search ................................. 424/424, 425, 424/426

[56] References Cited

FOREIGN PATENT DOCUMENTS 0279666  8/1988  European Pat. Off. .

Primary Examiner—Peter F. Kulkosky
Attorney, Agent, or Firm—Oblon, Spivak, McClelland, Maier & Neustadt, P.C.

[57] ABSTRACT

A bio-degradable/absorbable barrier membrane is coated thereon with sucrose esters of fatty acids. The sucrose esters of fatty acids is one or more members selected from the group consisting of monoester, diester, and polyester. The fatty acid is one or more members selected from the group consisting of stearic acid, palmitic acid, lauric acid, and myristic acid. These higher fatty acids may be mixed with a lower fatty acid.

4 Claims, No Drawings

BIO-DEGRADABLE/ABSORBABLE BARRIER MEMBRANE

BACKGROUND OF THE INVENTION

The present invention relates to a bio-degradable/absorbable barrier membrane for the regeneration of tissue, which can effectively be used for the guide of tissue or other purposes in medical fields such as dentistry and oral surgery.

GTR techniques (Guided Tissue Regeneration technique) for regenerating the periodontal ligament by use of a barrier membrane which blocks other tissue that inhibits growth of the periodontal ligament and so ensures a space allowing for growth of the periodontal ligament, are generally adopted in dentistry. In implantation therapies, too, GBR techniques (Guided Bone Regeneration technique) have recently been introduced. Teflon membranes are used as such barrier membranes with some outcome, but they must be removed by a second operation after insertion by first operation for the therapy, because they are a foreign matter to a living body and response to tissue. This is a serious burden on both clinicians and patients.

In recent years, bio-degradable/absorbable synthetic polymer materials or collagen have been used as a bio-degradable/absorbable barrier membrane in place of such nonabsorbable Teflon membranes. Exemplary bio-degradable/absorbable synthetic polymer materials include lactide/glycolide copolymers, lactide homopolymers, lactide/ε-caprolactone copolymers.

A bio-degradable/absorbable barrier membrane must have the following properties:

- it must come into a ready close contact with and fit to the surface of a tooth and inhibits in-growth of the epithelium,
- it must have a certain strength or a constant modulus of elasticity that ensures to allow for a space for new attachment,
- it must have a porous structure through which body fluids such as nutritious matter pass and which imparts some flexibility thereto, and
- it must enable blood to be discriminated from the oral tissue, even when deposited thereon.

The bio-degradable/absorbable barrier membrane must also be kept in shape until the periodontal ligament is regenerated. Moreover, just after the periodontal ligament is regenerated, it must be degraded and absorbed by the living body to vanish with no trace thereof left in the living body.

In the case of the conventional bio-degradable/absorbable barrier membranes, however, much difficulty is involved in controlling the physical properties inclusive of strength and the in vivo ability to hydrolyze, i.e., bio-degradable/absorbable rate. In particular, this barrier membrane is indicated to have some serious problems, for instance, the tearing of the membrane during suture, which is caused by a decrease in strength due to the permeation of blood through it, difficulty involved in discriminating the membrane from the oral tissue when it is discolored by the permeation of blood through it, and the permeation of cells into fine pores which are enlarged by biological degradation and absorption. Thus, no satisfactory material has been reported as yet.

An object of the present invention is therefore to eliminate the defects of the above-mentioned conventional bio-degradable/absorbable barrier memberane and so provide a bio-degradable/absorbable barrier membrane which is substantially free from the above-mentioned problems which arise in connection with the tearing of the membrane during suture, which is caused by a decrease in strength due to the permeation of blood, difficulty involved in discriminating the membrane from the oral tissue when it is discolored by the permeation of blood, and the permeation of cells into fine pores which are enlarged by biological degradation and absorption.

According to the present invention accomplished as a result of intensive studies made so as to achieve the above-mentioned object, it has now been found that if a bio-degradable/absorbable barrier membrane such as the one above mentioned is coated on the surface with sucrose esters of fatty acids to control its dynamic properties and its bio-degradable/absorbable rate, its in vivo degradation is delayed and the rate of permeation of blood through it is so inhibited that the tearing thereof during suture can be prevented and the discrimination thereof from the oral tissue can be ensured.

DETAILED EXPLANATION OF THE INVENTION

The sucrose esters of fatty acids used herein are ester of sucrose and a fatty acid, and may be in the form of monoester and/or diester and/or polyester, and any one of these esters can be used alone or in combination. The fatty acid used herein is preferably selected from the group consisting of stearic acid, palmitic acid, lauric acid, and myristic acid, which may be used alone or in combination of two or more. For use, such higher fatty acids may be mixed with lower fatty acids such as acetic acid, and butyric acid. Such sucrose esters of fatty acids are now widely used in the form of food additives, e.g., emulsifiers, foaming agents, and dispersants, and found to be of great safety.

In the present invention, a porous bio-degradable/absorbable barrier membrane is used. This barrier membrane is coated on the surface with the sucrose esters of fatty acids by dipping it in a hexane solvent with the sucrose esters of fatty acids dissolved therein and then volatilizing off the solvent. Any desired solvent, e.g., alcohol or heptane, may be used as well, with the proviso that the sucrose esters of fatty acids, not the barrier membrane, is dissolved therein. The amount of the sucrose esters of fatty acids coated may be varied by altering the concentration of the sucrose esters of fatty acids in the solvent. At low concentrations, however, coating may be done twice or more. Preferably, the sucrose esters of fatty acids should be coated on the barrier membrane in the minimum amount needed to impart the desired performance thereto. That amount can readily be determined by experimentation.

EXAMPLE

Example 1

The bio-degradable/absorbable barrier membrane used herein consisted of lactide/glycolide acid copolymers and had an average pore size of 23 μm. In the sucrose esters of fatty acids used herein, the fatty acid moiety consisted of stearic acid and palmitic acid. The barrier membrane was coated with the sucrose esters of fatty acids by dipping it in a 10 wt % solution of the sucrose esters of fatty acids in a hexane solvent, and then volatilizing off the solvent, thereby preparing a barrier membrane having a (mean) pore size of 20 μm.

Example 2

The barrier membrane used herein was the same as used in Example 1, and the sucrose esters of fatty acids used herein consisted of stearic acid, palmitic acid and acetic in DMEM with 10% of bovine fetus's serum added thereto for one week together with the thus immersed samples, using a cell permeation testing machine (Product name-:"Ten-Hole Chemotaxis Chamber" made by Neuro Probe Co., Ltd. and sold by Ieda Boeki Co., Ltd.). Following this, the cells were immobilized with 2% para-formaldehyde and stained with hematoxylin to observe the cells deposited on the back sides of the lactide/glycolide copolymer membrane samples under an inverted microscope. The number of the cells was counted by means of a grid ($1\times1$ mm$^2$) to find the rate of cell permeation by [(Number of cells deposited on the sample surface)/(Number of originally seeded cells)]×100

TABLE 1

| | Tensile strength (kgf/mm$^2$) | | Appearance testing | Rate of cell permeation (%) | | | |
|---|---|---|---|---|---|---|---|
| | Before immersion in blood | Five minutes after immersion in blood | Five minutes after immersion in blood | After three days | After seven days | After fifteen days | After twenty-one days |
| Example 1 | 3.7 | 3.6 | No discoloration | 0 | 0 | 0 | 5 |
| Example 2 | 3.8 | 3.7 | No discoloration | 0 | 0 | 1 | 6 |
| Comparative Example | 2.7 | 1.9 | Reddish | 0 | 8 | 15 | 34 | acid. As mentioned in Example 1, the barrier membrane was coated to obtain a barrier membrane having a (mean) pore size of 20 μm.

Comparative Example 1

An bio-degradable/absorbable barrier membrane consisting of the same lactide/glycolide copolymer as mentioned in Example 1 and having a (mean) pore size of 20 μm was prepared. However, this was not coated with the sucrose esters of fatty acids.

The barrier membranes according to Examples 1 and 2 as well as Comparative Example 1 were used to determine their appearance, tensile strength, and cell permeation. The results are shown in Table 1.

Tensile strength testing was carried out at cross head speed of 100 mm/min., a temperature of 25° C. and a relative humidity of 65%, using a universal testing machine (Tensilon/UTM-4-100 made by Toyo Balldwin Co., Ltd.).

Sample size was 5 cm in length, 1 cm in width and 200 μm in thickness. The samples were measured before and five minutes after immersion in the blood of a dog. For appearance testing, the permeation of blood into the tensile testing samples after immersion for five minutes was visually observed.

To examine a change (enlargement) of fine pores due to bio-degradable/absorbable, cell permeation testing was carried out in the following procedures. Samples, each obtained by cutting a bio-degradable/absorbable barrier membrane to a length of 2 cm, a width of 2 cm and a thickness of 200 μm, were immersed in DMEM with 10% of bovine fetus's serum added thereto for 3, 7, 15, and 21 days respectively. Thereafter, culture cells ($5.2\times10^3$ $pieces$) were seeded and cultured As can be seen from Table 1, the bio-degradable/absorbable barrier membrane according to the present invention shows neither substantial decrease in tensile strength even after immersion in blood nor discoloration due to the permeation of blood into it, and has an effect upon delaying the permeation of cells considerably. Thus, the bio-degradable/absorbable barrier membrane according to the present invention is much superior to the comparative example (untreated).

Since the bio-degradable/absorbable barrier membrane according to the present invention as above explained in detail is coated thereon with the sucrose esters of fatty acids, there is no drop in strength after the permeation of blood through it, and so the present barrier membrane has no risk of being torn during suture. Moreover, the present barrier membrane shows no discoloration due to the permeation of blood through it, and is well controlled in terms of the rate at which it is degraded and absorbed by a living body so that enlargement of fine pores due to bio-degradation/absorption can be prevented over a certain period of time; so it can have a significant effect on blocking cells. Thus, the present barrier membrane can be effectively used to regenerate tissues for guiding tissues or other purposes in medical fields such as dentistry and oral surgery and so makes a great contribution to medical fields such as dentistry and oral surgery.

What is claimed is:

1. A bio-degradable/absorbable sheet-like barrier member that is porous to blood and which is coated thereon with sucrose esters of fatty acids, said membrane comprising a synthetic polymer material or collagen, wherein the membrane shows reduced discoloration after immersion in blood.

2. The barrier membrane as recited in claim 1, wherein the sucrose esters of fatty acids is a mixture of one or more members selected from the group consisting of monoester, diester, and polyester.

3. The barrier membrane as recited in claim 2, wherein the fatty acid of sucrose esters of fatty acids is one or more members selected from the group consisting of stearic acid, palmitic acid, lauric acid, and myristic acid.

4. The barrier member as recited in claim 2, wherein the fatty acid of sucrose esters of fatty acids is a mixture of one or more members selected from the group consisting of stearic acid, palmitic acid, lauric acid, and myristic acid with a lower fatty acid.

* * * * *